US 8,406,489 B2

(12) United States Patent
Hirakawa

(10) Patent No.: US 8,406,489 B2
(45) Date of Patent: Mar. 26, 2013

(54) IMAGE DISPLAY APPARATUS

(75) Inventor: Katsumi Hirakawa, Tokyo (JP)

(73) Assignee: Olympus Medical Systems Corp (JP)

( * ) Notice: Subject to any disclaimer, the term of this patent is extended or adjusted under 35 U.S.C. 154(b) by 1188 days.

(21) Appl. No.: 11/571,412

(22) PCT Filed: Aug. 29, 2006

(86) PCT No.: PCT/JP2006/017005
§ 371 (c)(1),
(2), (4) Date: Dec. 28, 2006

(87) PCT Pub. No.: WO2007/029569
PCT Pub. Date: Mar. 15, 2007

(65) Prior Publication Data
US 2008/0292150 A1 Nov. 27, 2008

(30) Foreign Application Priority Data
Sep. 9, 2005 (JP) ................................ 2005-263089

(51) Int. Cl.
G06K 9/00 (2006.01)
G06K 9/34 (2006.01)
(52) U.S. Cl. ........................................ 382/128; 382/164
(58) Field of Classification Search .......... 382/128–132;
600/104, 113, 114, 476
See application file for complete search history.

(56) References Cited

U.S. PATENT DOCUMENTS

| | | | | |
|---|---|---|---|---|
| 5,241,302 A | * | 8/1993 | Thong | 345/589 |
| 2004/0225223 A1 | * | 11/2004 | Honda et al. | 600/476 |
| 2005/0025365 A1 | | 2/2005 | Oosawa | 382/218 |
| 2005/0165272 A1 | * | 7/2005 | Okada et al. | 600/114 |
| 2006/0140498 A1 | * | 6/2006 | Kudo et al. | 382/254 |

FOREIGN PATENT DOCUMENTS

| | | |
|---|---|---|
| CA | 2523302 | 11/2004 |
| EP | 1618828 | 1/2006 |
| JP | 2004-337596 | 12/2004 |
| WO | WO 02/21530 A1 | 3/2002 |
| WO | WO 2004/096025 | 11/2004 |

OTHER PUBLICATIONS

PCT Form 304 and Notification Concerning Availability of Publication issued in connection with corresponding PCT Appln. No. PCT/JP2006/317005 dated Mar. 15, 2007.

(Continued)

Primary Examiner — Amara Abdi
(74) Attorney, Agent, or Firm — Ostrolenk Faber LLP

(57) ABSTRACT

An image display apparatus 4 includes a control unit 15 having an image display controller 15a and an image processing controller 15b to enable an easy recognition of a condition and the like of an imaging target with respect to respective image areas at each imaging point. The image display controller 15a controls to display a time scale indicating an imaging period of a series of intra-subject images, to divide a display area of each time point on the time scale so as to be associated with divided image areas, and to display average colors of divided image areas respectively in divided scale areas separated as a result of the division, the divided scale areas and the divided image areas being associated with each other, respectively. The image processing controller 15b obtains image data stored in the portable recording medium 5 or the storage unit 14 to output to an image processor 13, and controls various image processes on the output image.

9 Claims, 9 Drawing Sheets

OTHER PUBLICATIONS

International Search Report PCT/JP2006/317005 dated Nov. 14, 2006 (Japanese Patent Office).

Search Report issued by European Patent Office in connection with corresponding application No. EP 06 79 6982 on Sep. 3, 2010.

* cited by examiner

1

IMAGE DISPLAY APPARATUS

CROSS REFERENCE TO RELATED APPLICATION

The present application is a 35 U.S.C. §§371 national phase conversion of PCT/JP2006/317005, filed 29 Aug. 2006, which claims priority of Japanese Patent Application No. 2005-263089 filed 9 Sep. 2005, which is herein incorporated by reference.

The present invention relates to an image display apparatus for displaying a series of images captured at multiple time points, specifically to an image display apparatus which is suitable for displaying a series of intra-subject images captured by using a capsule endoscope inserted in the subject.

BACKGROUND ART

In recent years, a swallowable capsule endoscope has been developed in the field of an endoscope. The capsule endoscope having an imaging function and a radio communication function is inserted from a mouth into a body of a subject for an observation, and travels to capture images of the inside of organs such as the stomach, the small intestine, and the large intestine according to their peristalsis until it is naturally excreted.

While the capsule endoscope travels inside the organs, image data captured by the capsule endoscope in the subject body is sequentially transmitted to the outside of the subject by a radio signal to be stored in a memory provided in a receiver placed outside of the subject, or displayed on a display provided to the receiver. A doctor, a nurse, or the like can make a diagnosis based on images displayed on a display based on the image data stored in the memory, or images displayed on the display provided to the receiver simultaneously with the receiver's data reception.

Since the number of a series of images captured by the capsule endoscope is usually enormous, the doctor, nurse, or the like needs a great amount of time and effort to observe the enormous number of images and make a diagnosis. In response to such a circumstance, an image display apparatus, which has an improved image search performance and enables an easy recognition of what organ the image on the display captures, has been proposed (see Patent Document 1, for example).

The image display apparatus displays a time scale which indicates an imaging period of the series of images, and also displays time-series average colors of respective images on the time scale. Since the average colors of the images correspond to captured-organ-specific colors, respectively, the doctor, nurse, or the like can easily recognize, by observing the average color displayed on the time scale, what organ the images at respective imaging time points capture.

Patent Document 1: Japanese Patent Application Laid-Open No. 2004-337596

DISCLOSURE OF INVENTION

Problem to be Solved by the Invention

However, since the image display apparatus described above is configured to calculate average color of a whole image area with respect to each image, there has been a problem that, when an area of importance is present at a part of an image area, for example, a bleeding site and the like is present at a part of the image area, it is difficult to recognize the presence of the area of importance based on the average color of the image area. Consequently, there has been a problem of having a possibility that the image capturing the area of importance may be overlooked when images are searched and determined based on an observation of the average color.

In view of the foregoing, an object of the present invention is to provide an image display apparatus which is capable of displaying a feature of a series of images captured at multiple time points with respect to each display area having a plurality of image areas over an entire imaging period, and enables an easy recognition of a condition and the like of an imaging object with respect to respective image areas of each image captured at each imaging time point.

Means for Solving Problem

An image display apparatus according to one aspect of the present invention is for displaying a series of images captured at multiple time points and a time scale indicating an imaging period of the series of images, and includes an average color calculator that calculates area average-colors of respective divided image areas prepared by dividing each image among the series of images into predetermined image areas; and a display controller that controls to display the area average-colors of divided image areas that are associated with respective divided scale areas, on the divided scale areas which are prepared by dividing a display area of each time point on the time scale in association with the respective divided image areas.

In the image display apparatus according to the invention, the area average-colors may be period-area average-colors obtained by averaging the area average-colors of a plurality of images for each divided image areas over a predetermined partial imaging period.

In the image display apparatus according to the present invention, the respective divided image areas may be formed by dividing each image into a predetermined dividing direction, and the display controller may control to divide a display area at each time point on the time scale in the same direction as the dividing direction, and to display one of the area average-colors and the period-area average-colors of divided image areas associated with the respective divided scale areas, on the respective divided scale areas associated with the respective divided image areas in the divided order.

In the image display apparatus according to the present invention, the respective divided image areas may be formed by dividing each image into four in a lateral direction and a vertical direction on a display screen, and the display controller may control to divide a display area of each time point on the time scale into four in the lateral direction and the vertical direction on the display screen, and to display one of the area average-colors and the period-area average-colors of divided image areas associated with the respective divided scale areas, on the respective divided scale areas associated with the respective divided image areas in the divided order.

The image display apparatus according to the present invention, may include a feature-area detector that detects a feature image area having a predetermined feature among the respective divided image areas of the each image, wherein the average color calculator may weight differently between color information in the feature image area and color information in each of the divided image areas other than the feature image area respectively, and may calculate an averaged weighted-area average-color as the area average-color.

In the image display apparatus according to the present invention, the weighted-area average-color may be a period-area average-color obtained by averaging the weighted-area average-colors of a plurality of images for the every divided image areas in a predetermined partial imaging period.

In the image display apparatus according to the present invention, the average color calculator may weight differently between the weighted-area average-colors of the feature images containing the feature image area and the area average-colors of a plurality of images other than the feature images in the partial imaging period, and may calculate a weighted-period-area average-color average as the period-area average-colors.

In the image display apparatus according to the present invention, the average color calculator may calculate the period-area average-color by using a series of images in a predetermined sampling period of the partial imaging period.

In the image display apparatus according to the present invention, the average color calculator may calculate the area average-color by using color information of each pixel at a predetermined sampling interval in the divided image areas.

In the image display apparatus according to the present invention, the series of images may be intra-subject images captured by using a capsule endoscope inserted in a subject.

Effect of the Invention

The image display apparatus according to the present invention is capable of displaying a feature of a series of images captured at multiple time points with respect to each display area having a plurality of image areas over an entire imaging period, and enables an easy recognition of a condition and the like of an imaging object with respect to respective image areas of each image captured at each imaging time point.

EXPLANATIONS OF LETTERS OR NUMERALS

1 SUBJECT
2 CAPSULE ENDOSCOPE
3 RECEIVING DEVICE
4 IMAGE DISPLAY APPARATUS
5 PORTABLE RECORDING MEDIUM
6 RECEIVING ANTENNA
6a to 6h ANTENNAS
11 INPUT UNIT
12 DISPLAY UNIT
13 IMAGE PROCESSOR
13a AVERAGE COLOR CALCULATOR
14 STORAGE UNIT
15 CONTROL UNIT
15a IMAGE DISPLAY CONTROLLER
15b IMAGE PROCESSING CONTROLLER
21 WINDOW
22 MAIN DISPLAY AREA
23 MAIN DISPLAY IMAGE
24 ANTENNA ARRANGEMENT PLAN
25 IMAGE OPERATION AREA
26 COLOR BAR
26a to 26d DIVIDED COLOR BARS
27 TIME BAR
27a SLIDER
28 DISPLAY SUBAREA

BEST MODE(S) FOR CARRYING OUT THE INVENTION

Exemplary embodiments of a radio system for acquiring intra-subject information as a preferred embodiment of an image display apparatus according to the present invention will be explained in detail with reference to the accompanying drawings. However, the present invention shall not be limited to the embodiments. Throughout the drawings, the same part is denoted by the same numeral.

FIRST EMBODIMENT

Figure 1:
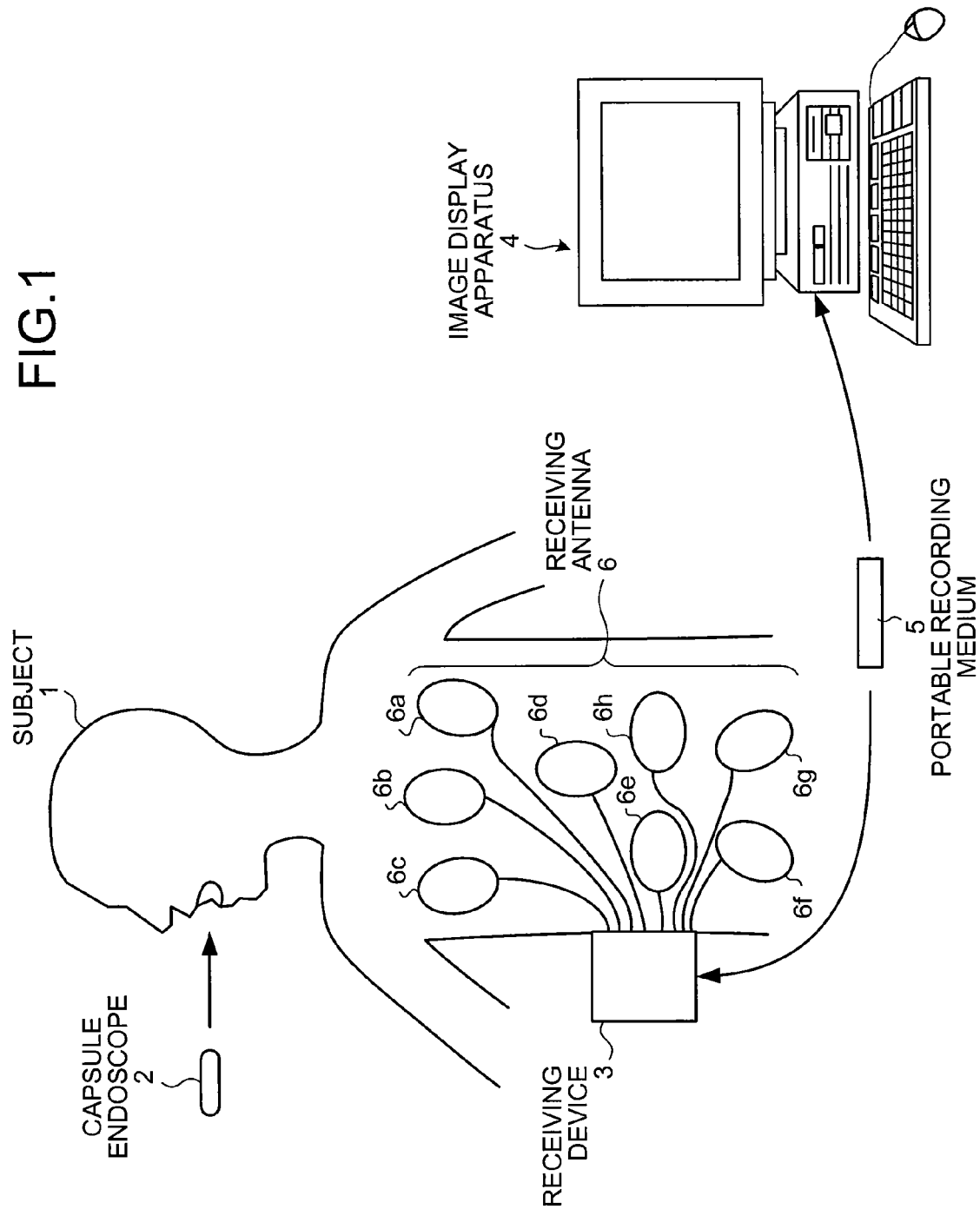
FIG. 1 is a schematic diagram of a configuration of a radio system for acquiring intra-subject information according to a first embodiment.

First, a radio system for acquiring intra-subject information provided with an image display apparatus according to a first embodiment will be explained. FIG. 1 is a schematic diagram of an entire configuration of the radio system for acquiring intra-subject information. The radio system for acquiring intra-subject information uses a capsule endoscope as one example of a body-insertable device.

As shown in FIG. 1, the radio system for acquiring intra-subject information includes a capsule endoscope 2 which is inserted into a body of a subject 1 to wirelessly transmit image data of a captured intra-subject image to a receiving device 3; the receiving device 3 which receives the image data wirelessly transmitted from the capsule endoscope 2; an image display apparatus 4 which displays the intra-subject image based on an image signal received by the receiving device 3; and a portable recording medium 5 which transfers image data and the like between the receiving device 3 and the image display apparatus 4.

The receiving device 3 include a receiving antenna 6 having a plurality of antennas 6a to 6h which are attached on an outside surface of the subject 1. The receiving device 3 receives image data and the like wirelessly transmitted from the capsule endoscope 2 via the receiving antenna 6, and records every piece of the received image data so as to associate with reception intensity information of respective antennas 6a to 6h at the time of data reception.

The antennas 6a to 6h realized by a loop antenna for example, are disposed at predetermined positions on the outside surface of the subject 1, i.e., positions respectively corresponding to organs as a path of the capsule endoscope 2 inside the subject 1. The antennas 6a to 6h may be arranged at predetermined positions on a jacket or the like to be worn by the subject 1. In this case, the antennas 6a to 6h are arranged at predetermined positions on the outside surface of the subject 1 through the jacket or the like. An arrangement of the antennas 6a to 6h may be changed arbitrarily depending on the purposes such as an observation, a diagnosis, or the like of the subject 1. The number of antennas provided to the receiving antenna 6 is not necessarily limited to eight as explained here as antennas 6a to 6h, and may be less or more than eight.

The image display apparatus 4 realized by a work station having a cathode-ray tube (CRT), a liquid crystal display, or the like for example, displays an image based on image data obtained via the portable recording medium 5 or the like. The image display apparatus 4 may output the image data to an output device such as a printer. The image display apparatus 4 has a function of communicating with an external device, and obtains/outputs the image data via wired or radio communication.

The portable recording medium 5 realized by a compact flash (registered trademark) memory, CD, DVD and the like, is detachable with respect to the receiving device 3 and the image display apparatus 4, and can record or output various types of information such as the image data and the like when the portable recording medium 5 is attached to the receiving device 3 and the image display apparatus 4. For example, the portable recording medium 5 is attached to the receiving device 3 and records the image data and the like transmitted from the capsule endoscope 2 to the receiving device 3, while the capsule endoscope 2 travels inside the subject 1. After the capsule endoscope 2 is discharged from the subject 1, the portable recording medium 5 is removed from the receiving device 3 and attached to the image display apparatus 4 to output the recorded image data and the like to the image display apparatus 4. Since the image data is transferred between the receiving device 3 and the image display device 4 via the portable recording medium 5, the subject 1 can freely move while the capsule endoscope 2 is in the subject 1. The image data may be transferred through wired or radio communication between the receiving device 3 and the image display apparatus 4.

Figure 2:
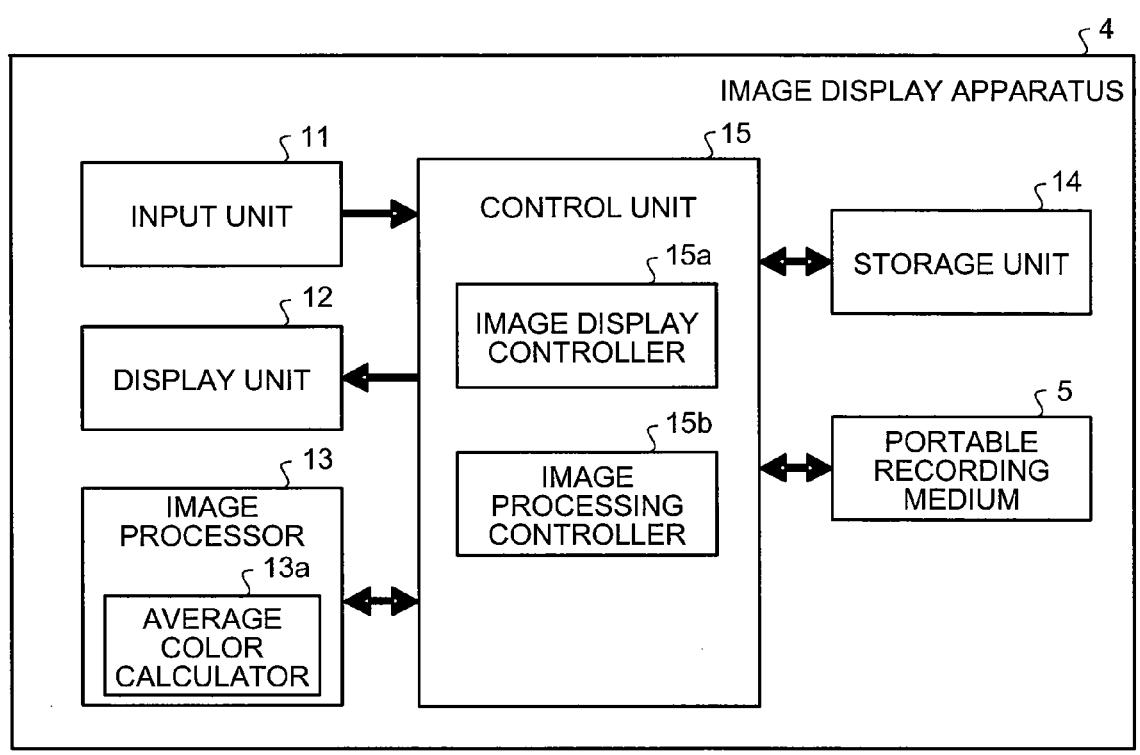
FIG. 2 is a block diagram of a configuration of an image display apparatus according to the first embodiment.

Next, a configuration of the image display apparatus 4 according to the first embodiment will be explained. FIG. 2 is a block diagram of a configuration of the image display apparatus 4. As shown in FIG. 2, the image display apparatus 4 includes an input unit 11 which allows inputting various types of information; a display unit 12 which displays the various types of information; an image processor 13 which processes the input image; a storage unit 14 which stores the various types of information; and a control unit 15 which controls the process and operation of each unit of the image display apparatus 4. The input unit 11, the display unit 12, the image processor 13, and the storage unit 14 each are electrically connected to the control unit 15. The image display apparatus 4 further includes an interface for the portable recording medium 5 so that the portable recording medium can be detachably equipped. The portable recording medium 5 is electrically connected to the control unit 15 when attached to the image display apparatus 4.

The input unit 11 includes various switches, an input key, a mouse, a touch screen, and the like, and inputs various types of information such as selection information of an image to be displayed. An observer of the displayed image as an operator of the image display apparatus 4 performs various operations of reading the displayed image, image selection, image recording and the like via the input unit 11. The input unit 11 may include an interface for wired or wireless communication such as a universal serial bus (USB), IEEE1394, or the like so that images can be input by an external device.

The display unit 12 includes a liquid crystal display and the like, and displays various types of information such as image data. Particularly, the display unit 12 displays various data such as image data stored in the portable recording medium 5 or the storage unit 14, and the Graphical User Interface (GUI) window which requests the observer or the like of the image display apparatus 4 to input various types of processing information.

The storage unit 14 is realized by a ROM in which various processing programs and the like are stored in advance, and a RAM which stores processing parameters for each process, processing data, and the like. The storage unit 14 can store image data input via the portable recording medium 5 and the like, image data processed by the image processor 13, display control data processed by an image display controller 15a, and the like.

The image processor 13 obtains image data from the portable recording medium 5 or the storage unit 14 based on a control by an image processing controller 15b, and performs various image processes on the obtained image data, such as a concentration conversion (gamma conversion and the like), a smoothing (noise elimination and the like), a sharpening (edge emphasis and the like), an image recognition (detection of feature image area, computing of an average color, and the like), and the like.

The image processor 13 includes an average color calculator 13a that calculates average colors of the series of input images. Specifically, the average color calculator 13a divides each of the series of images into a predetermined plural number of image areas, and calculates an area average-color as an average color by averaging color information of each pixel in respective divided image areas separated as a result of division. The average calculator 13a further calculates a period-area average-color by averaging area average-colors of respective divided image areas of a plurality of images among the series of images with respect to each of equivalent divided image areas in the images, per predetermined period of time, i.e., partial imaging period.

The control unit 15 is realized by a central processing unit (CPU) and the like which execute various processing programs stored in the storage unit 14.

Specifically, the control unit 15 includes the image display controller 15a and the image processing controller 15b. The image display controller 15a controls to display a series of images captured at multiple time points as image data stored in the portable recording medium 5 or the storage unit 14 on the display unit 12. As the series of images specifically in the first embodiment, a series of images which capture the inside of organs of the subject 1 at multiple time points are displayed.

Specifically, the image display controller 15a controls to display a time scale indicating an imaging period of the series of the intra-subject images, to divide a display area of each time point on the time scale so as to be associated with the divided image areas, and to display area average-colors or period-area average-colors of divided image areas, which are respectively associated with divided scale areas, in the divided scale areas separated as a result of the division.

More specifically, when the average color calculator 13a divides each image into a predetermined direction, the image display controller 15a divides the display area of each time point on the time scale in the same direction as the image division on the display screen of the time scale, and associates the divided scale areas with the divided image areas, respectively. The image display controller 15a then controls to display area average-colors or period-area average-colors of the divided image areas, which are respectively associated with the divided scale areas, in the divided scale areas.

In this case, when the average color calculator 13a divides each image into four in the vertical direction (lateral direction) on the display screen for example, the image display controller 15a accordingly divides the display area of each time point on the time scale into four in the vertical direction (lateral direction) on the display screen in the same manner and associates the divided scale areas with divided image areas respectively in the divided order. Specifically, equivalent left side areas and right sides areas (top level areas and bottom level areas) of the divided scale areas and the divided image areas are associated with each other, respectively. It is preferable that when the time scale is divided in the vertical direction (lateral direction), the time axis of the time scale is set to the vertical direction (lateral direction). It is also preferable that the number of division of the divided image areas and divided scale areas is four or so, however the number thereof is not necessarily limited to four.

The image processing controller 15b obtains image data stored in the portable recording medium 5 or the storage unit 14 to output to the image processor 13, and controls various image processes of the output image. The image processing controller 15b outputs the image data which is the result of processing in the image processor 13 to the storage unit 14 or the portable recording medium 5 for storage.

Figure 3:
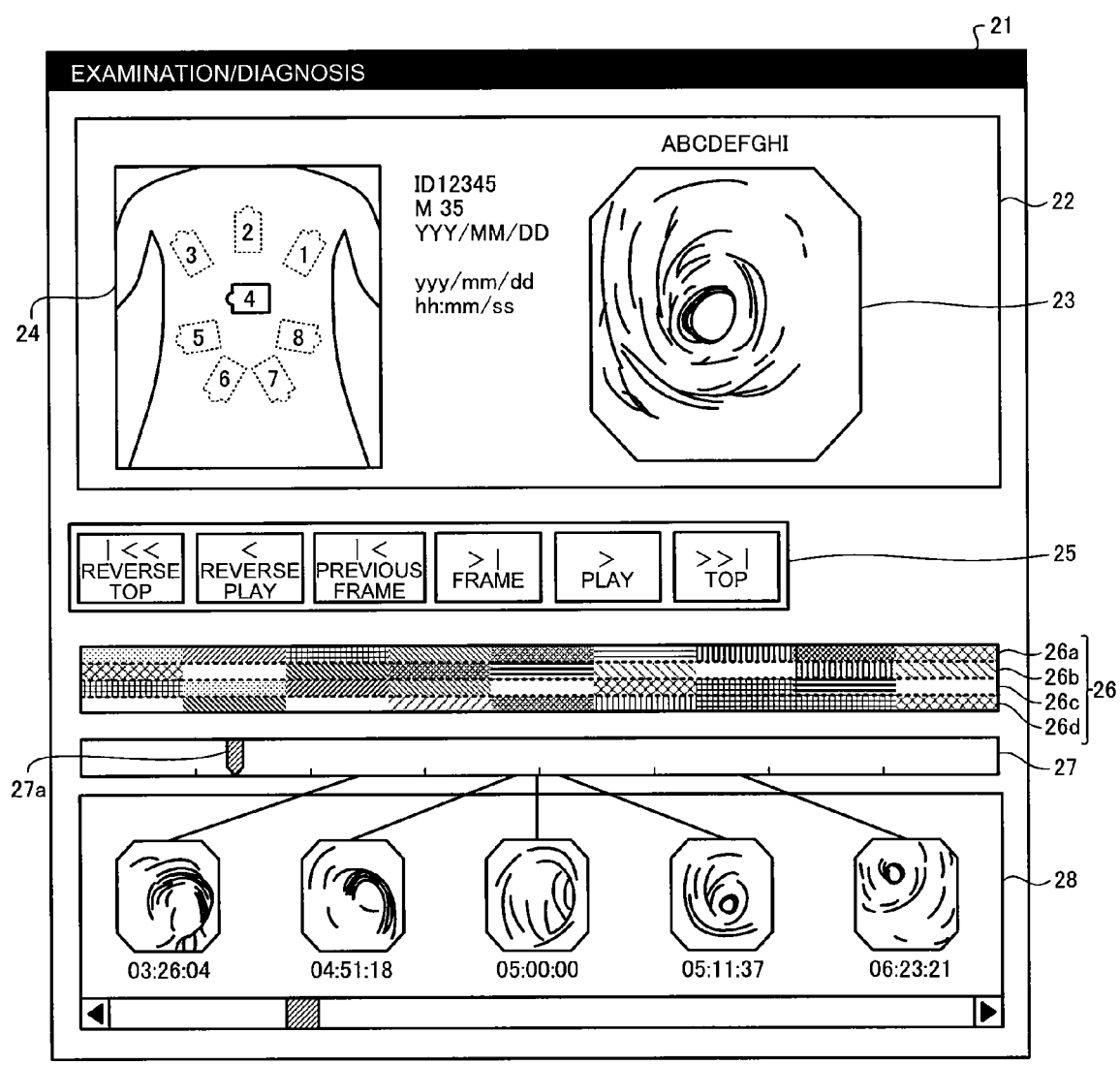
FIG. 3 illustrates a display screen image of the image display apparatus shown in FIG. 1.

Next, the display window (GUI window) which is displayed on the display unit 12 in the image display apparatus 4 will be explained. FIG. 3 illustrates one example of the GUI window displayed based on a control by the image display controller 15a in the image display apparatus 4. As shown in FIG. 3, the display unit 12 displays a window 21 ("Examination/Diagnosis" window) as the GUI window. The window 21 includes a main display area 22 which displays a main display image and the like; an image operation area 25 which has various image operation buttons shown as an icon; a color bar 26 and a time bar 27 as a time scale indicating an imaging period of the series of intra-subject images; and a display subarea 28 which exhibits a thumbnail and the like, each being arranged from top to bottom in parallel according to the order described above.

The main display area 22 exhibits a main display image 23 which is an image selected from the series of intra-subject images based on instruction information input by the input unit 11; and an antenna arrangement plan 24 which schematically illustrates an arrangement of the antennas 6a to 6h on the outside surface of the subject 1. The main display area 22 further includes textual information of name, ID number, sex, age, birth date, imaging date, imaging time, and the like of the subject 1, which is associated with the intra-subject image selected as the main display image 23. The main display area 22 can house predetermined two or more number of main display images according to a predetermined operation.

The antenna arrangement plan 24 schematically illustrates an arrangement of the antennas 6a to 6h together with a partial contour of the subject 1. In the antenna arrangement plan 24, an antenna number as an identification of each antenna is shown near each of the antennas 6a to 6h. In FIG. 3, numerals "1" to "8" are denoted for the antenna number, for example. In the antenna arrangement plan 24, the antenna which has maximum reception intensity among the antennas 6a to 6h when the intra-subject image displayed as the main display image 23 is captured, is exhibited discriminably from the other antennas. FIG. 3 illustrates a state where, as an antenna having maximum reception intensity, the antenna denoted by "4" is shown discriminably from the other antennas, for example. To realize a discriminative display, the image display controller 15a can control to display at least one of luminance, hue, and color saturation, of the antenna having the maximum reception intensity so as to be discriminable from the other antennas.

In the color bar 26, average colors of images in the series of intra-subject images are exhibited respectively in the time-series order as a whole. Specifically, a display area of each imaging time point on the color bar 26 indicates an average color of each intra-subject image captured at each imaging time point. Since the series of intra-subject images have organ-specific average colors respectively, the observer or the like can recognize the organ captured in the intra-subject image of each imaging time point based on the transition of the average colors along the time axis (lateral axis in FIG. 3) on the color bar 26.

The color bar 26 has a format where the entire display area thereof is divided into four in the lateral direction on the display screen. Divided color bars 26a to 26d of respective divided levels indicate time-series area average-colors or time-series period-area average-colors on respective levels, which respectively correspond to divided image areas of the series of intra-subject images. In other words, the average colors of respective intra-subject images are calculated with respect to each divided image area of the entire image area divided into four, and area average-colors or period-area average-colors of respective divided image areas which are respectively associated with the divided scale areas in the divided order, are displayed in the divided scale areas where the display area of each time point is divided into four in the lateral direction on the color bar 26.

According to the color bar 26, the observer or the like not only can estimate organs captured in intra-subject images at multiple time points, respectively based on the transition in the average colors along the time axis of the divided color bars 26a to 26d of respective levels, but also can easily recognize the detailed condition inside the captured organ depending on the divided image areas. Accordingly, when an average color of a red color group is visually recognized on a divided color bar 26a which is the top level of four levels for a certain period, for example, the observer or the like can recognize that a bleeding site is present inside the organ whose image is captured in the period, the bleeding site is present within the imaged range corresponding to the divided image areas on the top level of all intra-subject images in the period, and the like. Moreover, when an average color of a black color group in an image area including the luminal portion is displayed on a level of the divided color bars different from the level on which an average color of the other image areas is displayed, the observer or the like can recognize the condition of the inside of organs within the imaged range excluding the luminal portion.

A slider 27a which is movable in the time axis direction is displayed on the time bar 27. The slider 27a indicates an imaging time point of an intra-subject image displayed as a main display image 23 on the time bar 27, and moves on the time bar 27 in response to a changeover of the main display image 23. For example, when any one of image operation buttons in the image operation area 25 is operated via a mouse and the like (not shown), an image displayed as the main display image 23 is changed from one to another, and then the slider 27a moves to a position indicating the imaging time point of the intra-subject image displayed as the main display image 23 after the changeover.

In contrast, when the slider 27a is operated to move by the mouse and the like, an intra-subject image corresponding to an imaging time point which is indicated by the moved slider 27a is displayed as the main display image 23. When the slider 27a is operated to move in a row, images are each changed and displayed as the main display image 23 in a row correspondingly to the operations.

According to the slider 27a, the observer or the like can operate to move the slider 27a to an imaging time point corresponding to an intra-subject image of a desired organ which is picked out with reference to the color bar 26, so that the intra-subject image can be displayed immediately as the main display image 23.

The left ends of the color bar 26 and the time bar 27 as serving as a time scale, indicate an imaging time point of the first image of the time-series intra-subject images. The right ends thereof indicate an imaging time point of the last image of the time-series intra-subject images. Normally, the imaging time point at the left end corresponds to a start time point of image data reception by the receiving device 3, and the imaging time point at the right end corresponds to an end time point of the image data reception.

In the display subarea 28, an image selected and extracted from the series of intra-subject images is displayed as a thumbnail. Specifically, the intra-subject image displayed as the main display image 23 according to a predetermined button operation or mouse operation is additionally displayed in the display subarea 28 as the thumbnail, for example.

In the display subarea 28, each thumbnail has individual additional information such as imaging time displayed in the neighborhood as textual information. The additional information to be displayed as the textual information is variable according to a predetermined operation. It is also possible to hide the textual information. The display subarea 28 includes lines which associate thumbnails and imaging time points of the thumbnails shown on the time bar 27, respectively.

Since there is a limitation in the display area available for the display subarea 28, a batch display with up to a predetermined number of thumbnails can be allowed. FIG. 3, for example, illustrates a case where a batch display with up to five thumbnails is allowed. When the number of extracted thumbnails is greater than the predetermined number for the batch display, thumbnails over the predetermined number replace currently displayed thumbnails and are displayed in response to the operation of the scroll bar displayed in the display subarea 28. Each thumbnail displayed in the display subarea 28 is displayed as the main display image 23 in response to the predetermined button operation or mouse operation.

Figure 4:
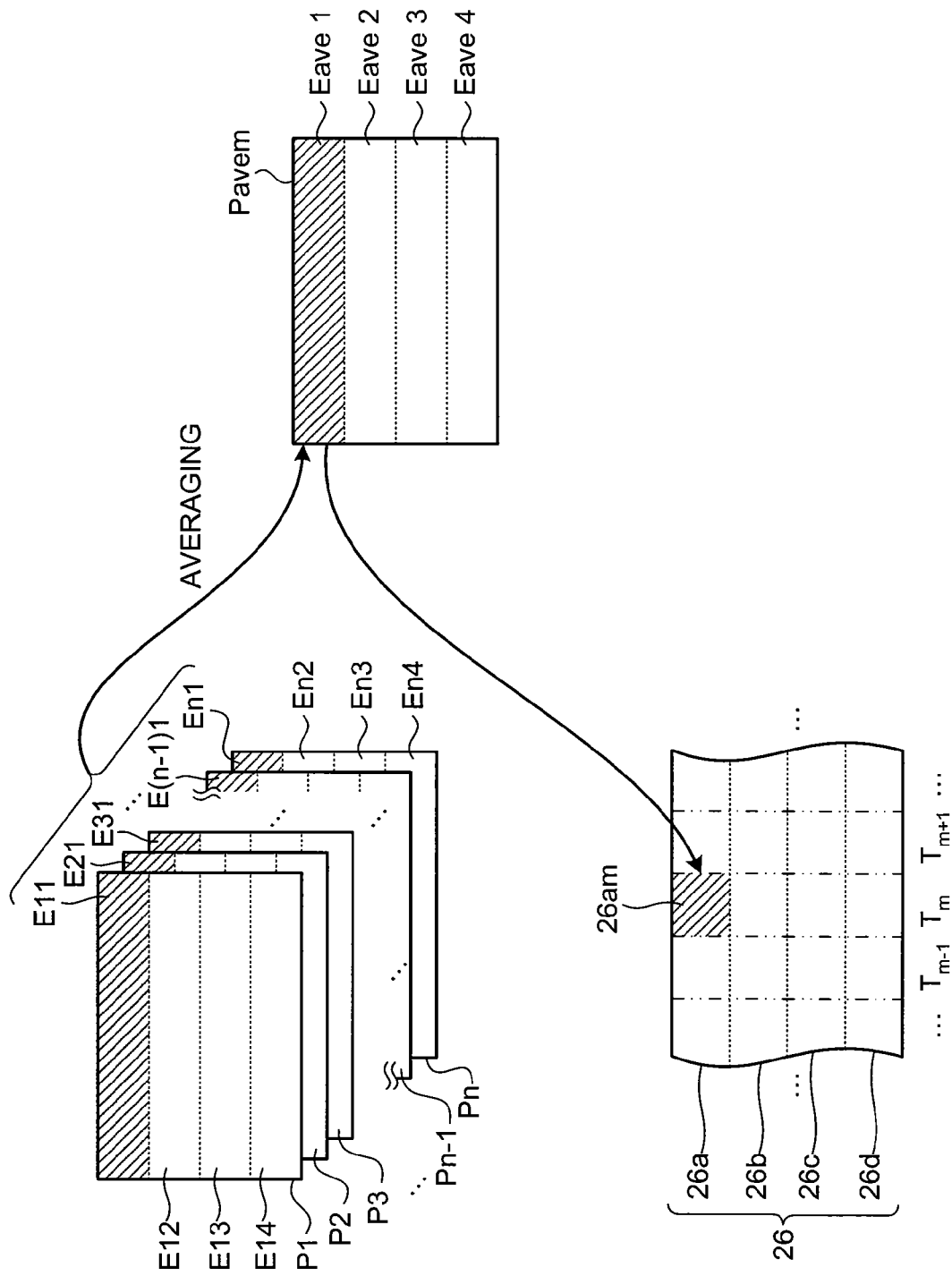
FIG. 4 is a diagram of a drawing process of the color bar shown in FIG. 3.

Here, a drawing process of the color bar 26 in the image display apparatus 4 according to the first embodiment will be explained. FIG. 4 is a conceptual diagram of a general procedure for drawing period-area average-color in a divided scale area 26am at a time point Tm on the color bar 26.

For the drawing of period-area average-colors on the color bar 26 as shown in FIG. 4, the image processing controller 15b first obtains a predetermined number of intra-subject images P1 to Pn in a predetermined partial imaging period corresponding to the time point Tm. Here, as the intra-subject images P1 to Pn, time-series consecutive images or a series of images extracted in a predetermined sampling period are selectively obtained. Which to be selected either the time-series consecutive images or the series of images extracted in a predetermined sampling period is arbitrarily variable depending on a predetermined operation. The image to be selected here may also be an image at one time point.

Subsequently, the image processing controller 15b controls the image processor 13 to divide each of the intra-subject images P1 to Pn into a plurality of divided image areas. For example, FIG. 4 illustrates a state where the intra-subject image P1 is laterally divided into four divided image areas E11 to E14, the intra-subject image Pn is divided into four divided image areas En1 to En4, and other intra-subject images of multiple time points during the period are divided into four divided image areas, respectively in the same manner.

Next, the image processing controller 15b controls the average color calculator 13a to calculate area average-colors of divided image areas of each of the intra-subject images P1 to Pn, respectively. At this point, the average color calculator 13a uses color information of all pixels of each divided image area or a plurality of pixels extracted at a predetermined sampling interval to calculate the area average-colors. Which to use for the calculation either all pixels of each divided image area or the plurality of pixels extracted at a predetermined sampling interval is arbitrarily variable depending on a predetermined operation.

Then, the image processing controller 15b performs averaging of area average-colors of divided image areas equivalent in each of the intra-subject images P1 to Pn, respectively, and calculates period-area average-colors. In other words, the image processing controller 15b calculates period-area average-colors by averaging area average-colors of the divided image areas on each level of four levels. Specifically, as for divided image areas E11, E21, E31, . . . E(n−1)1, En1 on the top level shaded with slash lines in FIG. 4, for example, the image processing controller 15b averages the area average-colors of these equivalent divided image areas and calculates a period-area average-color Eave1. In the same manner, area average-colors of groups of divided image areas E12 to En2; divided image areas E13 to En3; and divided image areas E14 to En4 on the other levels, are averaged to calculate period-area average-colors Eave2, Eave3, and Eave4, respectively.

The image processing controller 15b then associates the period-area average-colors Eave1 to Eave4 with divided image areas on the levels in the intra-subject images P1 to Pn, and the time point Tm, respectively, and then records in the storage unit 14 as average color group Pavem corresponding to the display area at the time point Tm on the color bar 26. The image processing controller 15b repeats such series of processes for every time point of the entire imaging period.

After the image processing controller 15b calculates all average colors of multiple time points to be drawn on the color bar 26, the image display controller 15a obtains a group of average colors of the multiple time points from the storage unit 14 to paint the divided scale areas of the multiple points in the period-area average-colors of divided image areas which are respectively associated with the divided scale areas. Specifically, in FIG. 4, the divided scale area 26am at the time point Tm of the divided color bar 26a on the top level is painted in the period-area average-color Eave1 which is calculated for the time point Tm by using divided image areas on the top level.

In the same manner, the image display controller 15a paints the divided scale areas of the multiple time points on the color bar 26 in the period-area average-colors of divided image areas associated by the image processing controller 15b, respectively. When the image selected as the predetermined number of intra-subject images P1 to Pn is one image at one time point, the period-area average-colors used in the drawing process is equal to the area average-colors of the image at the one time point.

Figure 5:
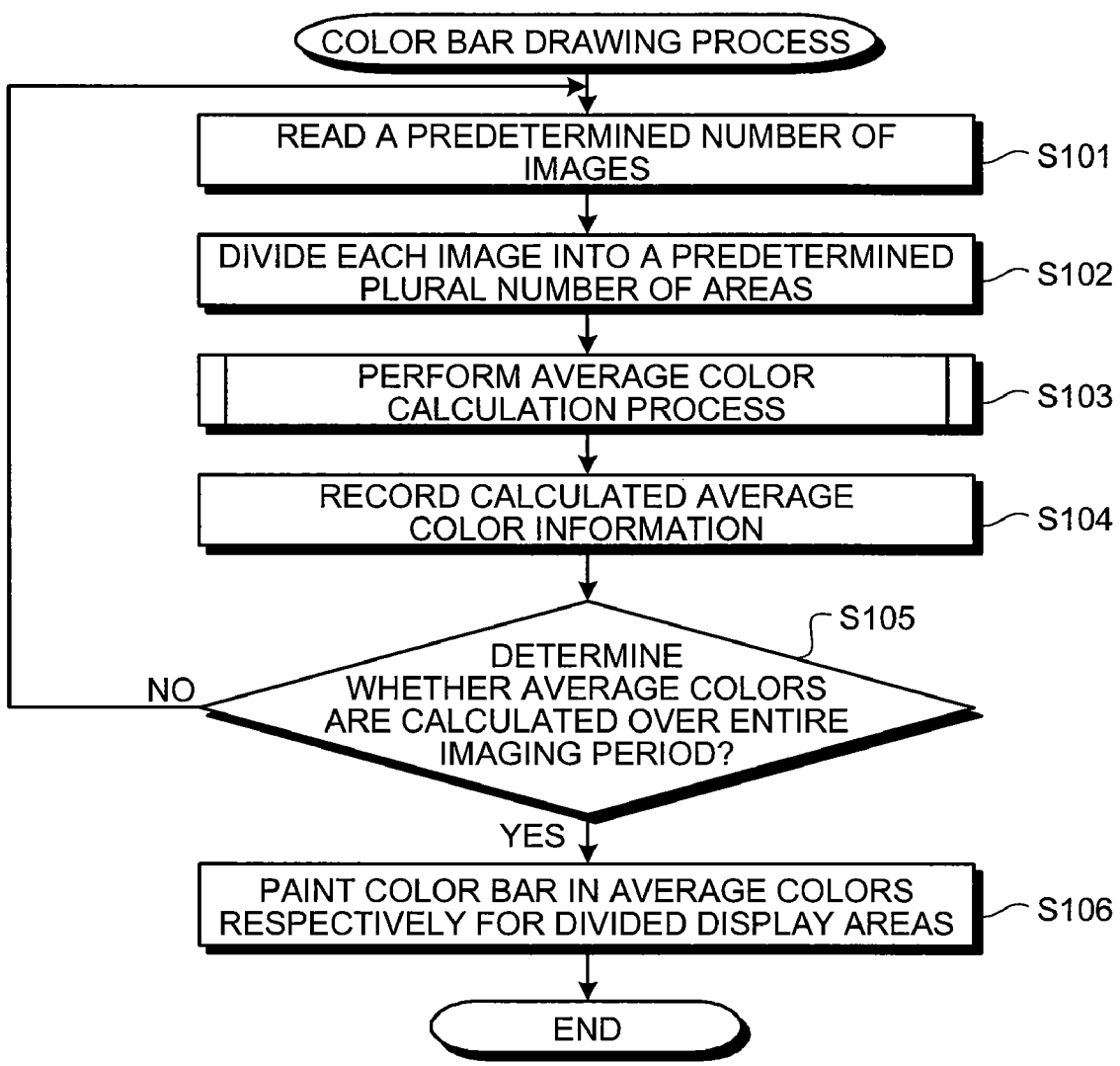
FIG. 5 is a flowchart of a procedure of the color bar drawing process performed by the image display apparatus shown in FIG. 1.

Here, a procedure of the drawing process of the color bar 26 performed in the image display apparatus 4 according to the first embodiment will be explained. FIG. 5 is a flowchart of the procedure of the drawing process of the color bar 26. As shown in FIG. 5, the image processing controller 15b reads a predetermined number of intra-subject images within a predetermined partial imaging period corresponding to the top time point of the time-series period among the series of intra-subject images stored in the portable recording medium 5 or the storage unit 14, and outputs to the image processing controller 13 (step S101).

Then, the image processing controller 15b controls the image processing controller 13 to divide each of the intra-subject images read at step S101 into a predetermined plural number of divided image areas (step S102). At step S102, each intra-subject image is, for example, divided into four divided image areas. Next, the image processing controller 15b controls the average color calculator 13a to calculate area average-colors of respective divided image areas divided at step S102, and performs an average calculation process in which area average-colors of all intra-subject images read at step S101 are averaged to calculate period-area average-colors (step S103).

The image processing controller 15b then associates the area average-color and the period-area average-color calculated at step S103 respectively with the time point as a processing target and the divided images on respective levels of the intra-subject image, and records the result in the storage unit 14 (step S104). The image processing controller 15b determines whether the average color calculation process over the entire imaging period is performed or not (step S105).

When the average colors of the entire imaging period are not calculated ("No" at step S105), the image processing controller 15b repeats the process from step S101 with respect to the time point whose average color is not calculated. On the other hand, when all average colors of the entire imaging period are calculated ("Yes" at step S105), the image processing controller 15b paints the color bar 26 per divided scale areas of a display area at each time point in the period-area average-colors associated therewith respectively (step S106), and ends the series of color bar drawing process.

Figure 6:
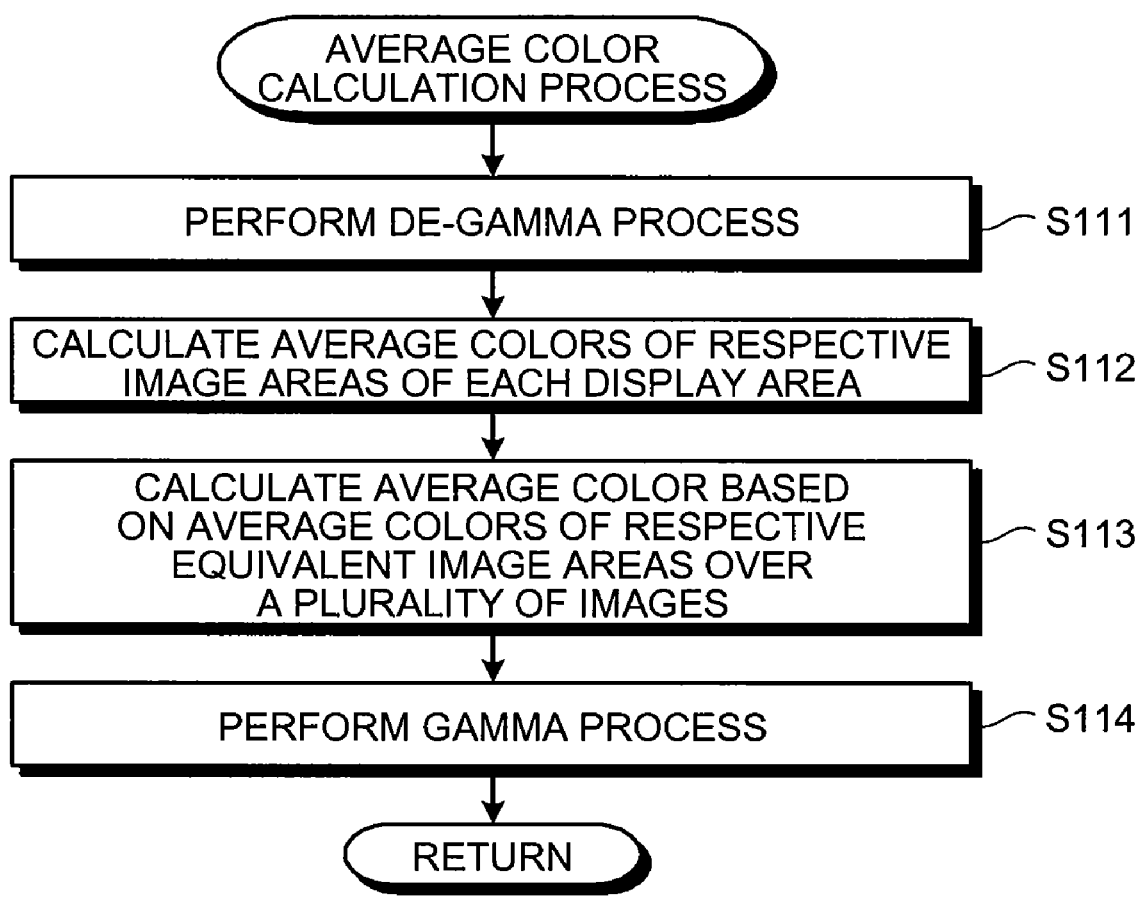
FIG. 6 is a flowchart of a procedure of the average color calculation process shown in FIG. 5.

Next, the average color calculator at step S103 will be explained. FIG. 6 is a flowchart of a procedure of the average color calculation process. As shown in FIG. 6, the average color calculator 13a first performs a de-gamma process on each intra-subject image as a processing target (step S111). Next, the average color calculator 13a calculates area average-colors of respective divided image areas of each intra-subject image (step S112), and calculates period-area average-colors by averaging area average-colors of all intra-subject images as a processing target (step S113). Subsequently, the average color calculator 13a performs a gamma process on the processing target of intra-subject images (step S114), and the process returns to step S103.

When the image read by the image processing controller 15b at step S101 is one intra-subject image at one time point, step S113 is skipped. In this case, the average color painted by the image display controller 15a at step S106 is the area average-color instead of a period-area average-color.

As explained above, in the image display apparatus 4 according to the first embodiment, the image display controller 15a controls to display the color bar 26 as a time scale, to divide a display area of each time point on the color bar 26 so as to be associated with the divided image areas, and to display area average-colors or period-area average-colors of divided image areas, which are respectively associated with the divided scale areas separated as a result of the division, in the divided scale areas. Accordingly, a feature of the series of intra-subject images captured at multiple time points can be displayed with respect to each of the display scale areas associated with the divided image areas respectively on the color bar 26 over the entire imaging period. Thus, it is possible for the observer or the like to easily recognize a condition and the like of the imaging target with respect to respective divided image areas at each imaging point.

SECOND EMBODIMENT

Next, a second embodiment according to the present invention will be explained. In the first embodiment described above, the intra-subject images are processed uniformly to calculate average colors. However, in the second embodiment, a feature area such as a bleeding site and the like contained in intra-subject images is weighted to calculate average colors.

Figure 7:
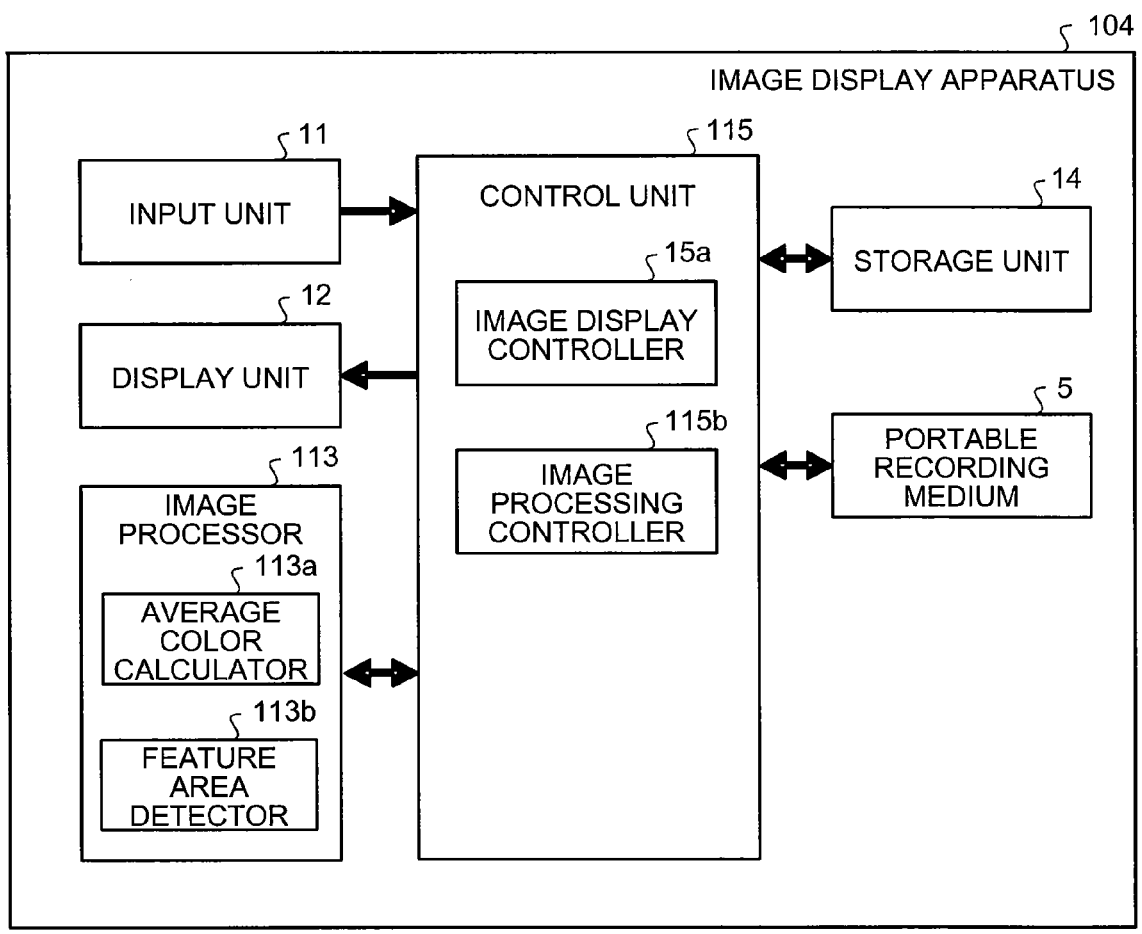
FIG. 7 is a block diagram of a configuration of an image display apparatus according to a second embodiment of the present invention.

FIG. 7 is a block diagram of a configuration of an image display apparatus 104 according to the second embodiment. As shown in FIG. 7, the image display apparatus 104, which is prepared based on the image display apparatus 4, has an image processor 113 and a control unit 115 in place of the image processor 13 and the control unit 15 of the image display apparatus 4, respectively. The image processor 113 includes an average color calculator 113a and a feature-area detector 113b. The control unit 115 includes an image processing controller 115b in place of the image processing controller 15b of the control unit 15. The other structures of the second embodiment are the same as the first embodiment, and such components are denoted by the same numerals.

The feature-area detector 113b detects a feature area as a feature image area having a predetermined feature among respective divided image areas of each of the input intra-subject images. In other words, the feature-area detector 113b identifies a predetermined feature such as a bleeding site and the like based on color information of each pixel constituting the intra-subject image for example to detect the feature area. The feature-area detector 113b may detect not only a bleeding site but also various sites suspected of being affected such as a discolored site, and an aberrantly-shaped site of the inside the organs as the feature area, for example. The feature-area detector 113b may detect the feature area based not only on the color information but also on various types of feature data such as a contour shape, a texture, and a concentration gradient.

The average color calculator 113a, similarly to the average color calculator 13a, calculates average colors of the series of input images. However, the average color calculator 113a weights the color information in a feature area detected by the feature-area detector 113b differently from color information in the divided image area excluding the feature area to calculate an weighted-area average-color averaged as an area average-color. The average color calculator 113a further calculates a period-area average-color by using the weighted-area average-color. Furthermore, the average color calculator 113a can weight the area average-color and the weighted-area average-color of the feature image containing the feature area differently from the area average-colors of multiple images excluding the feature image in the partial imaging period to calculate an average weighted-period-area color averaged as a period-area average-color.

Figure 8:
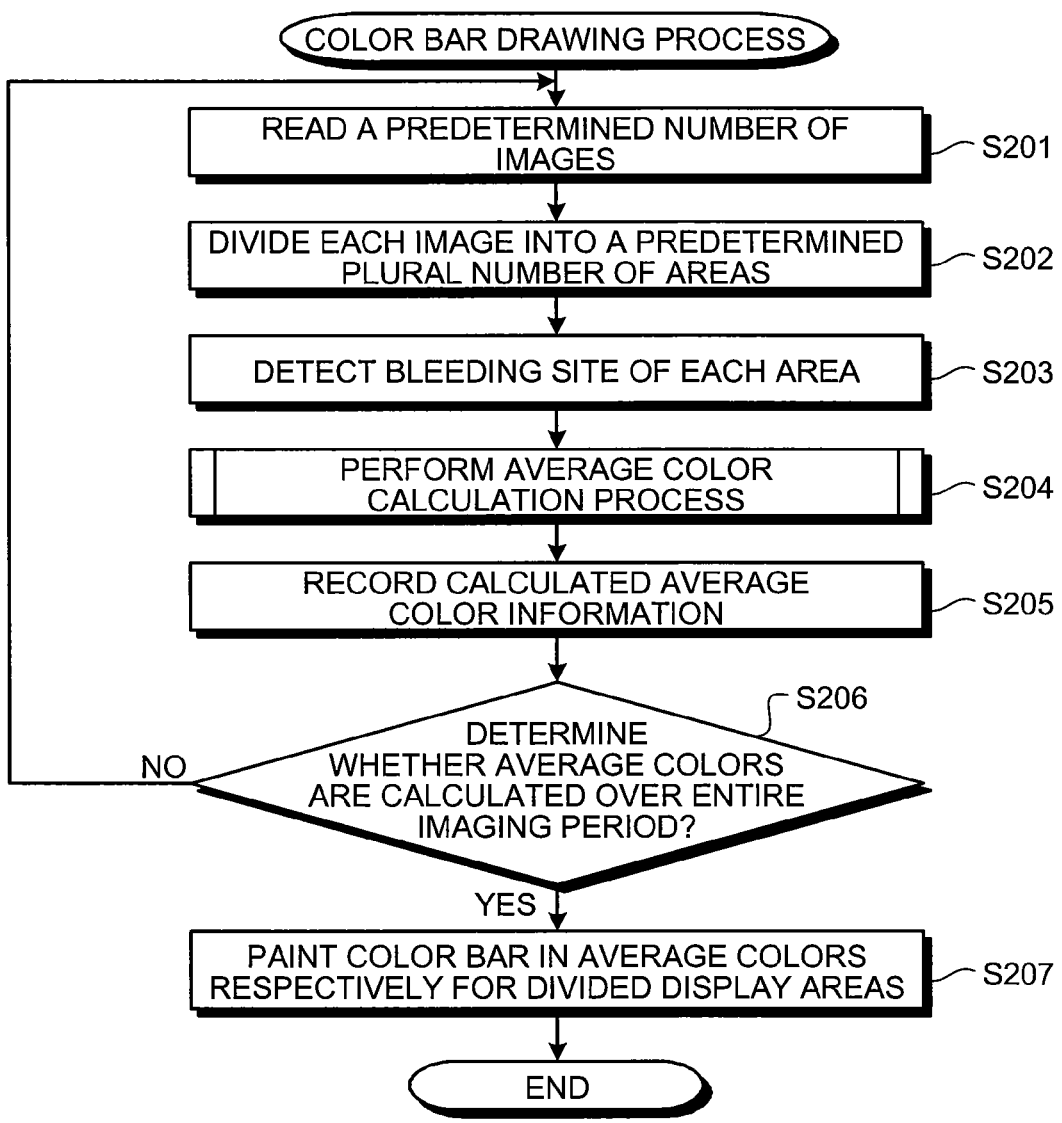
FIG. 8 is a flowchart of a procedure of a color bar drawing process performed by the image display apparatus shown in FIG. 7.

Here, a procedure of a drawing process of the color bar 26 performed by the image display apparatus 104 will be explained. FIG. 8 is a flowchart of the procedure of drawing process of the color bar 26. As shown in FIG. 8, the image processing controller 115b reads a predetermined number of intra-subject images within a predetermined partial imaging period corresponding to the top time point of the time-series period among the series of intra-subject images stored in the portable recording medium 5 or the storage unit 14, and outputs to the image processor 113 (step S201).

Then, the image processing controller 115b controls the image processor 113 to divide each of the intra-subject images read at step S201 into a predetermined plural number of divided image areas (step S202). At step S202, each intra-subject image is divided into four divided image areas, for example. Next, the image processing controller 115b controls the feature-area detector 113b to detect a feature area having a predetermined feature such as a bleeding site and the like from each of respective divided image areas divided at step S202 (step S203). Subsequently, the image processing controller 115b controls the average color calculator 113a to perform an average color calculation process for calculating average colors (step S204).

The image processing controller 115b then associates the average colors calculated at step S204 with the imaging time point of the processing target image and divided images on each level of the intra-subject image respectively, and stores in the storage unit 14 (step S205). The image processing controller 115b then determines whether the average color calculation process is performed over the entire imaging period or not (step S206).

When the average colors of the entire imaging period are not calculated ("No" at step S206), the image processing controller 115b repeats the process from step S201 for the time point whose average color is not calculated yet. On the other hand, when all average colors of the entire imaging period are calculated ("Yes" at step S206), the image processing controller 115b paints the color bar 26 per divided scale areas of a display area at each time point in average colors associated with the divided scale areas, respectively (step S207), and ends the series of color bar drawing process.

Figure 9:
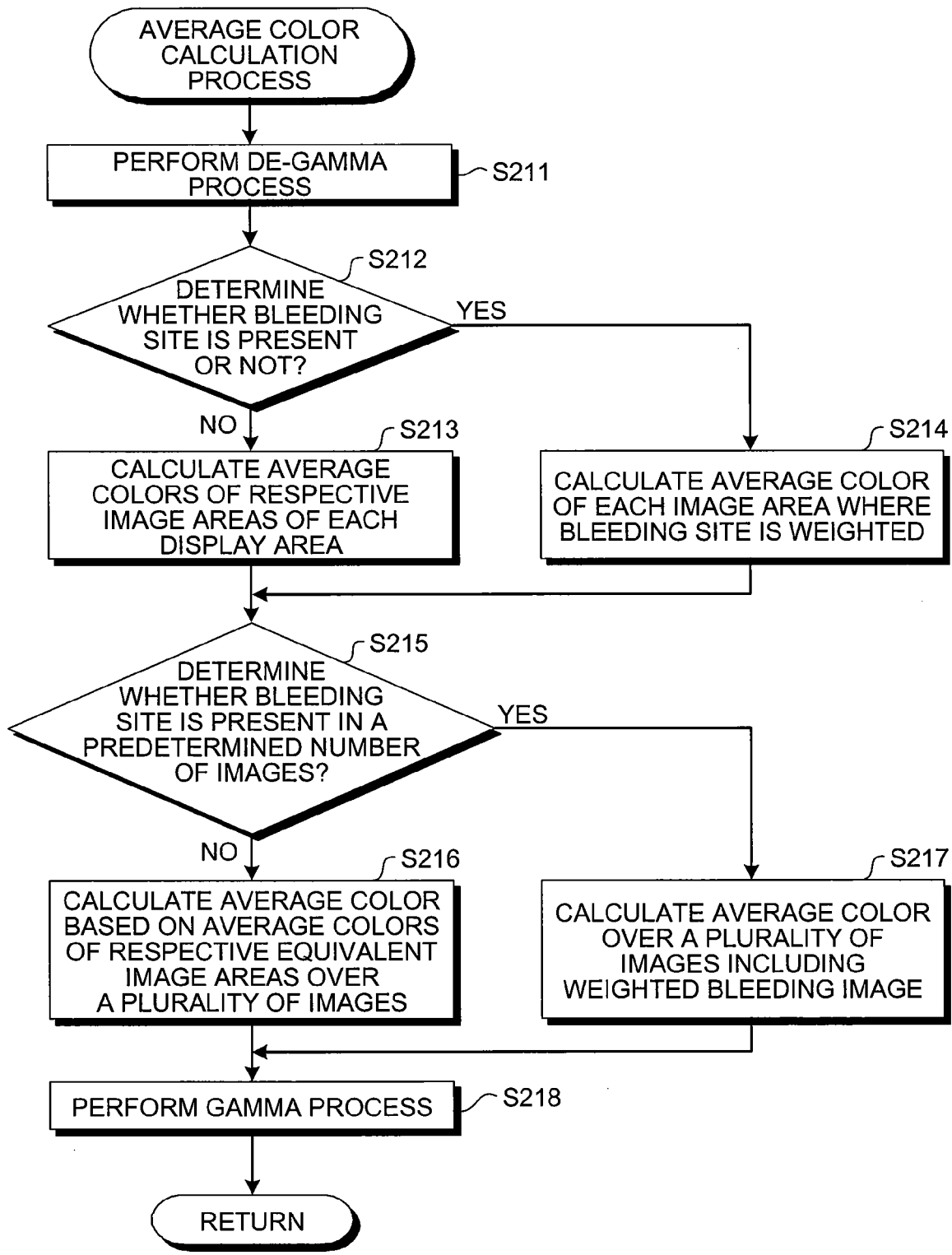
FIG. 9 is a flowchart of a procedure of the average color calculation process shown in FIG. 8.

Next, the average color calculator at step S204 will be explained. FIG. 9 is a flowchart of a procedure of the average color calculation process. The average color calculation process shown in FIG. 9 exemplifies a procedure of a case where a bleeding site is detected as the feature area at step S203.

As shown in FIG. 9, the average color calculator 113a performs a de-gamma process on each intra-subject image as a processing target (step S211), and determines whether there are any bleeding sites in respective divided image areas of each intra-subject image or not based on the detection result of the feature area at S203 (step S212). When no bleeding site is present ("No" at step S212), the average color calculator 113a, similarly to the step S112 shown in FIG. 6, calculates area average-colors of respective divided image areas of each intra-subject image (step S213).

On the other hand, when a bleeding site is present ("Yes" at step S214), the average color calculator 113a greatly weights color information in the feature area indicating each bleeding site compared with color information of the divided image area excluding the feature area, and calculates weighted-area average-color by averaging color information with respect to respective divided image areas (step S214). At step S214, the color information of the divided image area excluding the feature area may be zero-weighted, and the average weighted-area color may be calculated only by using color information in the feature area.

After step S213 or step S214, the average color calculator 113a determines whether there are any bleeding images containing a bleeding site among the predetermined number of processing target intra-subject images (step S215). When no bleeding image is present ("No" at step S215), the average color calculator 113a, similarly to step S113 shown in FIG. 6, calculates period-area average-colors by averaging area average-colors of all of the processing target intra-subject images (step S216).

On the other hand, when a bleeding image is present ("Yes" at step S215), the average color calculator 113a greatly weights area average-colors and weighted-area average-colors of respective bleeding images compared with the area average-colors of intra-subject images other than the bleeding images, and calculates weighted-period-area average-colors (step S217). At step S217, intra-subject images other than bleeding images may be zero-weighted, and the weighted-area average-color may be calculated only by using area average-color and weighted-area average-color of the bleeding image.

After step S216 or step S217, the average color calculator 113a performs a gamma process on each of the processing target intra-subject images (step S218), and the process returns to step S204.

When the image read by the image processing controller 115b at step S201 is one intra-subject image at one time point, steps S215 to S217 are skipped. In this case, the average color painted by the image display controller 115a at step S207 is equal to the area average-color or the weighted-area average-color.

As described above, in the image display apparatus 104 according to the second embodiment, the feature-area detector 113b detects a feature area having a predetermined feature such as a bleeding site and the like among respective divided image areas of each intra-subject image, and the average color calculator 113a weights at least one of the feature area and the feature image containing the feature area to calculate the weighted-area average-color as an area average-color and the period-area average-color as a period-area average-color. Thus, the image display controller 15a controls to display an average color which strongly reflects the presence of the feature area in respective divided scale areas on the color bar 26, and to display with an emphasis on the presence of the feature area for respective divided image areas of each imaging time point, and thereby enabling the observer or the like to more easily recognize a condition and the like peculiar to the imaging target. Thus, the observer or the like can further reduce the possibility of overlooking an image containing a feather area such as a bleeding site, i.e., an area of importance.

In the first and second embodiments described above, the series of images displayed in the image display apparatus 4 or 104 according to the present invention are explained as the series of intra-subject images which are captured by using the capsule endoscope 2 inserted into the subject 1. However, it is not necessarily limited to the intra-subject images, and may be any images of any subject as long as a series of images are captured at multiple time points by using any imaging device.

INDUSTRIAL APPLICABILITY

The image display apparatus according to the present invention is useful as an image display apparatus which displays a series of images captured at multiple time points, more specifically as an image display apparatus which displays a series of intra-subject images captured by using a capsule endoscope inserted in a subject.

The invention claimed is:
1. An image display apparatus for displaying a series of images captured at multiple time points and a time scale indicating an imaging period of the series of images, comprising:
   an average color calculator that calculates area average-colors, with a respective area average-color for each of a plurality of divided image areas, said divided image areas being prepared by dividing each image among the series of images in a lateral dividing direction on a display; and:

a display controller that is configured to cause two or more of the area average-colors of the divided image areas that are associated with respective divided image areas to be displayed on the display, the divided image areas being prepared by dividing a display area at each time point on the time scale in the lateral direction on the display so as to be associated with the respective divided image areas, wherein the divided image areas are arranged on the image display apparatus along said lateral direction and said lateral direction extends substantially perpendicular to an extending direction of the time scale.

2. The image display apparatus according to claim 1, wherein the area average-colors are period-area average-colors obtained by averaging the area average-colors of a plurality of images for each divided image areas over a predetermined partial imaging period.

3. The image display apparatus according to claim 1, wherein
the respective divided image areas are formed by dividing each image into four in a lateral direction and a vertical direction on the display screen, and
the display controller controls to divide a display area of each time point on the time scale into four in the lateral direction and the vertical direction on the display screen, and to display one of the area average-colors and the period-area average-colors of divided image areas associated with the respective divided scale areas, on the respective divided scale areas associated with the respective divided image areas in the divided order.

4. The image display apparatus according to claim 1, further comprising:

a feature-area detector that detects a feature image area having a predetermined feature among the respective divided image areas of the each image, wherein
the average color calculator weights differently between color information in the feature image area and color information in each of the divided image areas other than the feature image area respectively, and calculates an averaged weighted-area average-color as the area average-color.

5. The image display apparatus according to claim 4, wherein the weighted-area average-color is a period-area average-color obtained by averaging the weighted-area average-colors of a plurality of images for the every divided image areas in a predetermined partial imaging period.

6. The image display apparatus according to claim 5, wherein the average color calculator weights differently between the weighted-area average-colors of the feature images containing the feature image area and the area average-colors of a plurality of images other than the feature images in the partial imaging period, and calculates a weighted-period-area average-color averaged as the period-area average-colors.

7. The image display apparatus according to claim 1, wherein the average color calculator calculates the period-area average-color by using a series of images in a predetermined sampling period of the partial imaging period.

8. The image display apparatus according to claim 1, wherein the average color calculator calculates the area average-color by using color information of each pixel at a predetermined sampling interval in the divided image areas.

9. The image display apparatus according to claim 1, wherein the series of images are intra-subject images captured by using a capsule endoscope inserted in a subject.

* * * * *

UNITED STATES PATENT AND TRADEMARK OFFICE
CERTIFICATE OF CORRECTION

PATENT NO. : 8,406,489 B2
APPLICATION NO. : 11/571412
DATED : March 26, 2013
INVENTOR(S) : Katsumi Hirakawa Page 1 of 1

It is certified that error appears in the above-identified patent and that said Letters Patent is hereby corrected as shown below:

Title Page, item (86) should read,

(86) PCT No. PCT/JP2006/317005
§371 (c)(1),
(2), (4) Date: Aug. 29, 2006

Signed and Sealed this
Seventeenth Day of September, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,406,489 B2 | Page 1 of 1 |
| APPLICATION NO. | : 11/571412 | |
| DATED | : March 26, 2013 | |
| INVENTOR(S) | : Katsumi Hirakawa | |

It is certified that error appears in the above-identified patent and that said Letters Patent is hereby corrected as shown below:

This certificate supersedes the Certificate of Correction issued September 17, 2013. The certificate is vacated since request was filed in error by patentee. The patent is reinstated to its originally-issued form.

Title Page, Item (86)

--(86) PCT No.: PCT/JP2006/017005
              § 371 (c)(1),
                 (2)(4) Date: December 28, 2006--

Title Page, Item (86)

"(86) PCT No.: PCT/JP2006/017005"
should correctly read --(86) PCT No.: PCT/JP2006/317005--

Signed and Sealed this
Nineteenth Day of November, 2013

Teresa Stanek Rea
*Deputy Director of the United States Patent and Trademark Office*

UNITED STATES PATENT AND TRADEMARK OFFICE
CERTIFICATE OF CORRECTION

PATENT NO.        : 8,406,489 B2
APPLICATION NO.   : 11/571412
DATED             : March 26, 2013
INVENTOR(S)       : Katsumi Hirakawa Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1353 days.

Signed and Sealed this
First Day of September, 2015

Michelle K. Lee
*Director of the United States Patent and Trademark Office*